(12) United States Patent
Sitek et al.

(10) Patent No.: US 11,963,790 B2
(45) Date of Patent: Apr. 23, 2024

(54) ESTIMATING SPINAL AGE

(71) Applicant: Merative US L.P., Ann Arbor, MI (US)

(72) Inventors: Arkadiusz Sitek, Ashland, MA (US); Mark D. Bronkalla, Waukesha, WI (US); Larissa Christina Schudlo, Boston, MA (US); Benedikt Graf, Charlestown, MA (US); Yiting Xie, Cambridge, MA (US)

(*) Notice: Subject to any disclaimer, the term of this patent is extended or adjusted under 35 U.S.C. 154(b) by 802 days.

(21) Appl. No.: 16/952,459

(22) Filed: Nov. 19, 2020

(65) Prior Publication Data

US 2022/0151547 A1 May 19, 2022

(51) Int. Cl.
*A61B 5/00* (2006.01)
*G06T 7/00* (2017.01)

(52) U.S. Cl.
CPC .......... *A61B 5/4566* (2013.01); *G06T 7/0012* (2013.01); *G06T 2207/10081* (2013.01); *G06T 2207/10088* (2013.01); *G06T 2207/20081* (2013.01); *G06T 2207/20084* (2013.01); *G06T 2207/30012* (2013.01)

(58) Field of Classification Search
CPC ................ A61B 5/4566; G06T 7/0012; G06T 2207/10081; G06T 2207/10088; G06T 2207/20081; G06T 2207/20084; G06T 2207/30012
See application file for complete search history.

(56) References Cited

U.S. PATENT DOCUMENTS

| | | |
|---|---|---|
| 2003/0065264 A1 | 4/2003 | Tsoref |
| 2012/0065514 A1 | 3/2012 | Naghavi |
| 2015/0005680 A1 | 1/2015 | Lipani |
| 2017/0273593 A1 | 9/2017 | Kiraly |
| 2017/0293859 A1 | 10/2017 | Gennadievich |
| 2019/0088360 A1 | 3/2019 | Goble |
| 2019/0295727 A1 | 9/2019 | Xanthakis |
| 2019/0370957 A1 | 12/2019 | Manickam |
| 2020/0020097 A1 | 1/2020 | Do |

FOREIGN PATENT DOCUMENTS

| | | | |
|---|---|---|---|
| CN | 108836338 | * | 11/2018 |
| CN | 109118487 A | | 1/2019 |
| KR | 101961215 B1 | | 3/2019 |
| KR | 2020-0121608 | * | 10/2020 |
| WO | WO 2015/050929 | * | 4/2015 |

(Continued)

OTHER PUBLICATIONS

Machine translation for KR 2020-0121608 (Year: 2020).*

(Continued)

*Primary Examiner* — Qian Yang
(74) *Attorney, Agent, or Firm* — Stephen J. Walder, Jr.

(57) ABSTRACT

An approach for a computer program to receive image data of a subject including at least a portion of a spine of the subject and a chronological age of the subject. The approach includes the computer program pre-processing the image data including at least a portion of a spine. The approach includes determining an apparent age of the spine or a portion of the spine of the subject using a trained artificial intelligence deep learning algorithm.

20 Claims, 9 Drawing Sheets

(56) References Cited

FOREIGN PATENT DOCUMENTS

WO    2018131044    7/2018

OTHER PUBLICATIONS

Machine translation for CN 108836338 (Year: 2018).*
Andrew et al. "Spine Magnetic Resonance Image Segmentation Using Deep Learning Techniques", 2020 6th International Conference on Advanced Computing & Communication Systems (ICACCS) (Year: 2020).*
Anonymous et al., "Vascular age: You're only as old as your arteries", University of Wisconsin-Madison News, Sep. 26, 2003, 3 Pages.
Rensing, Bernadette., "Smoking Cigarettes Can Be a Chronic Pain in Your Neck", AAP Annual Meeting, Feb. 2016, 3 Pages.
Bakthula et al., "Automated human bone age assessment using image processing methods-survey." International Journal of Computer Applications, 104, No. 13, 2014, 10 Pages.
Grandvalet et al., "Semi-supervised Learning by Entropy Minimization", A Publication of the IST Programme of the European Community under the PASCAL Network of Excellence, IST-2002-506778, 2006, 8 Pages.
Khan et al., "Neural Network Based Spinal Age Estimation Using Lumbar Spine Magnetic Resonance Images (MRI)," 2013 4th International Conference on Intelligent Systems, Modelling and Simulation, Bangkok, 2013, pp. 88-93, doi: 10.1109/ISMS.2013.101, 6 Pages.
Reed et al., "Training Deep Neural Networks on Noisy Labels With Bootstrapping", Accepted as a workshop contribution at ICLR 2015, arXiv preprint, arXiv:1412.6596v3, [cs.CV], Apr. 15, 2015, 11 Pages.
Somkantha et al., "Bone age assessment in young children using automatic carpal bone feature extraction and support vector regression." Journal of Digital Imaging, 24(6), 1044-1058, 2011, 15 Pages.
Spampinato et al., "Deep learning for automated skeletal bone age assessment in X-ray images." Medical Image Analysis, 36: 41-51, 2017, 39 Pages.
Štern et al., "Automated age estimation from hand MRI volumes using deep learning." In International Conference on Medical Image Computing and Computer-Assisted Intervention (pp. 194-202). Springer, Cham. Oct. 2016, 8 Pages.
Sukhbaatar et al., "Training Convolutional Networks With Noisy Labels", Accepted as a workshop contribution at ICLR 2015, arXiv preprint, arXiv:1406.2080v4, [cs.CV], Apr. 10, 2015, 11 Pages.
Zhou et al., "Using Convolutional Neural Networks and Transfer Learning for Bone Age Classification," 2017 International Conference on Digital Image Computing: Techniques and Applications (DICTA), Sydney, NSW, pp. 1-6, 2017, 6 Pages.

* cited by examiner

ESTIMATING SPINAL AGE

BACKGROUND

The present invention relates generally to the field of computer data processing, and more particularly to a method to train a machine learning algorithm as a functional spine age prediction model using unsupervised deep learning.

Spinal degeneration manifests as changes to the spinal column that cause changes in the normal spine structure and/or spine function. Typically, back pain is the most common symptom of spinal degeneration. Back pain from spinal degeneration ranges from mild or none in some patients to debilitating in other patients. Traditionally, one or more of several treatment options involving stretching and exercises for the patient are prescribed to reduce back pain or to prevent the worsening of spinal degenerative changes in the patient. In some cases, patients experience a reduction of back pain caused by spinal degeneration through the use of one or more of heat treatment, pain relief drugs, such as nonsteroidal anti-inflammatory drugs, acupuncture, or physiotherapy with spinal manipulation.

SUMMARY

Embodiments of the present provide a method, a computer program product, and a computer system for one or more computer processors to receive image data of a subject including at least a portion of a spine of the subject and a chronological age of the subject. The method includes the computer processors pre-processing the image data including at least a portion of a spine and determining an apparent age of one of the spine or a portion of the spine of the subject using a trained artificial intelligence deep learning algorithm.

3C is an illustration of a two-dimensional section of a vertebra, in accordance with at least one embodiment of the invention.

Figure 4:
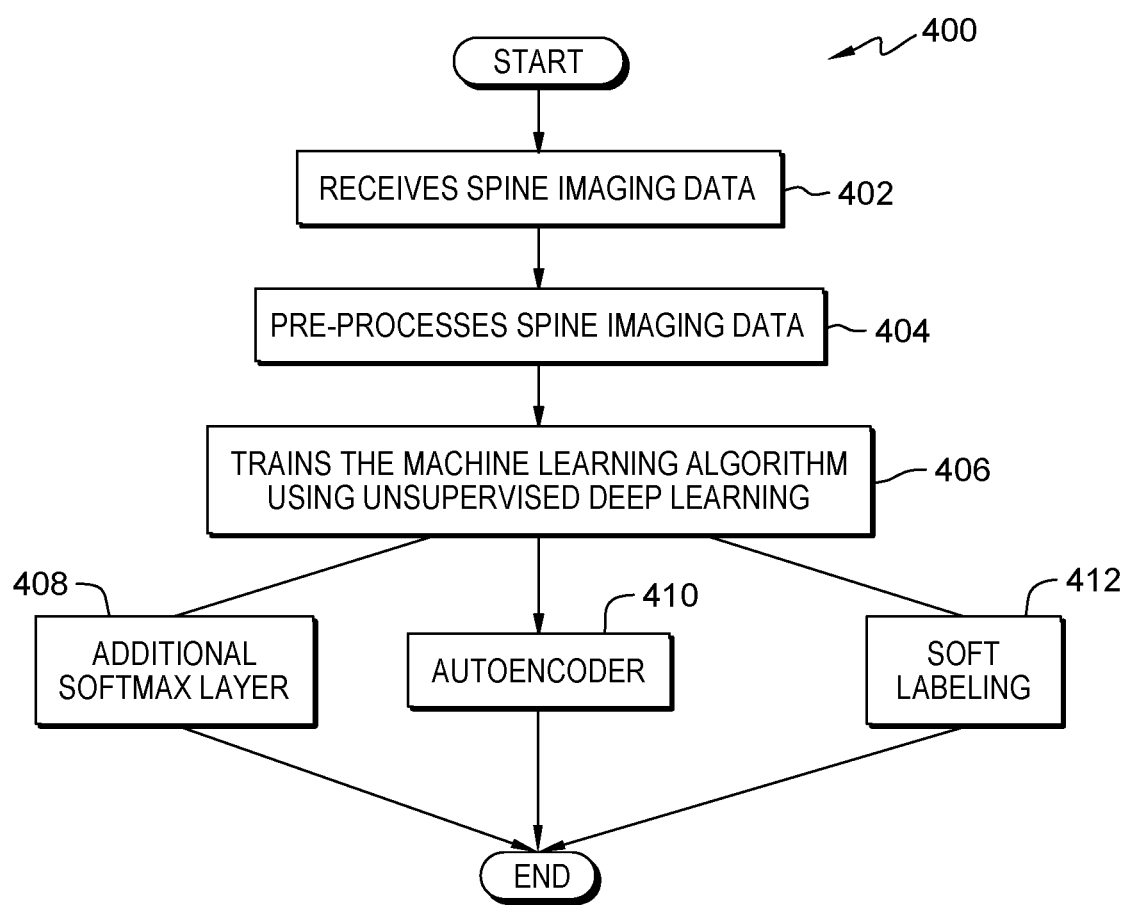

FIG. 4 is an example of a program flow chart diagram depicting operational steps for training the apparent spine age program, in accordance with at least one embodiment of the invention.

Figure 5:
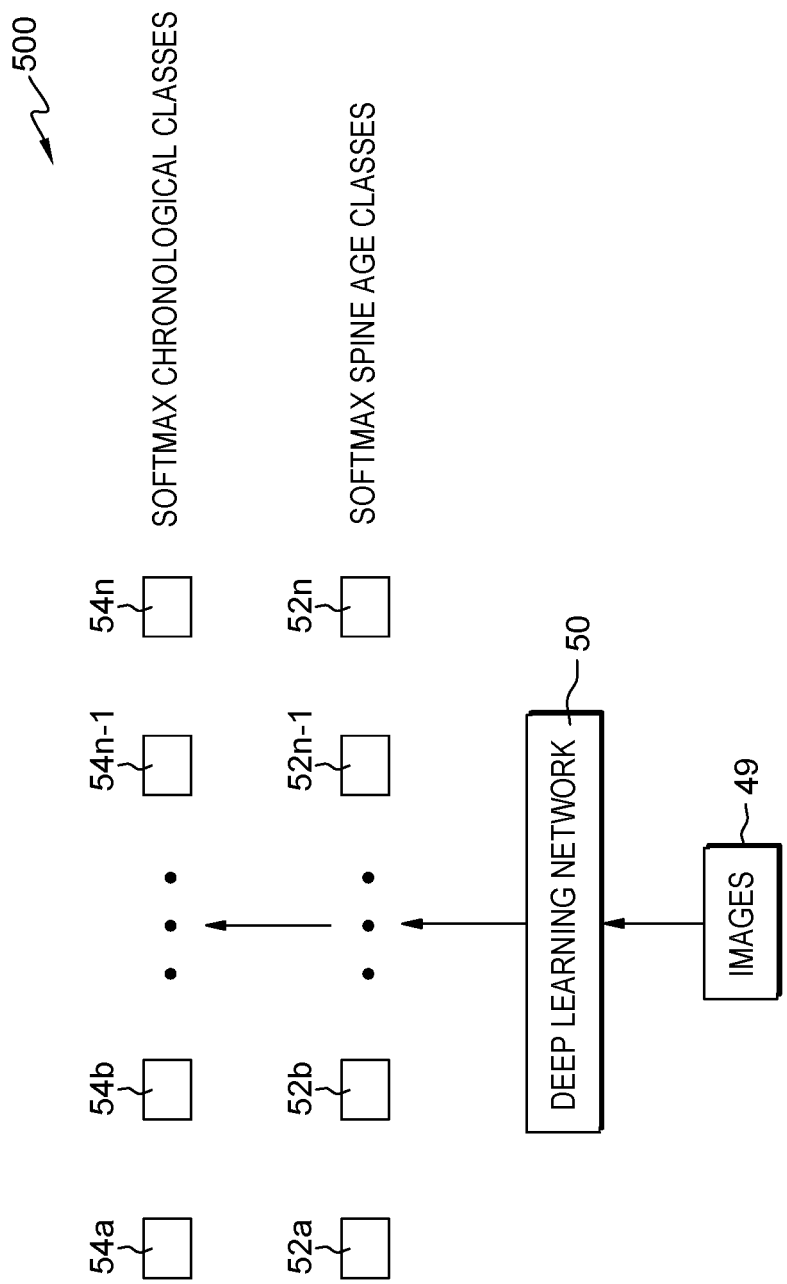

FIG. 5 is a schematic diagram of a method of unsupervised deep learning for training the apparent spine age program using an additional softmax layer, in accordance with at least one embodiment of the invention.

Figure 6:
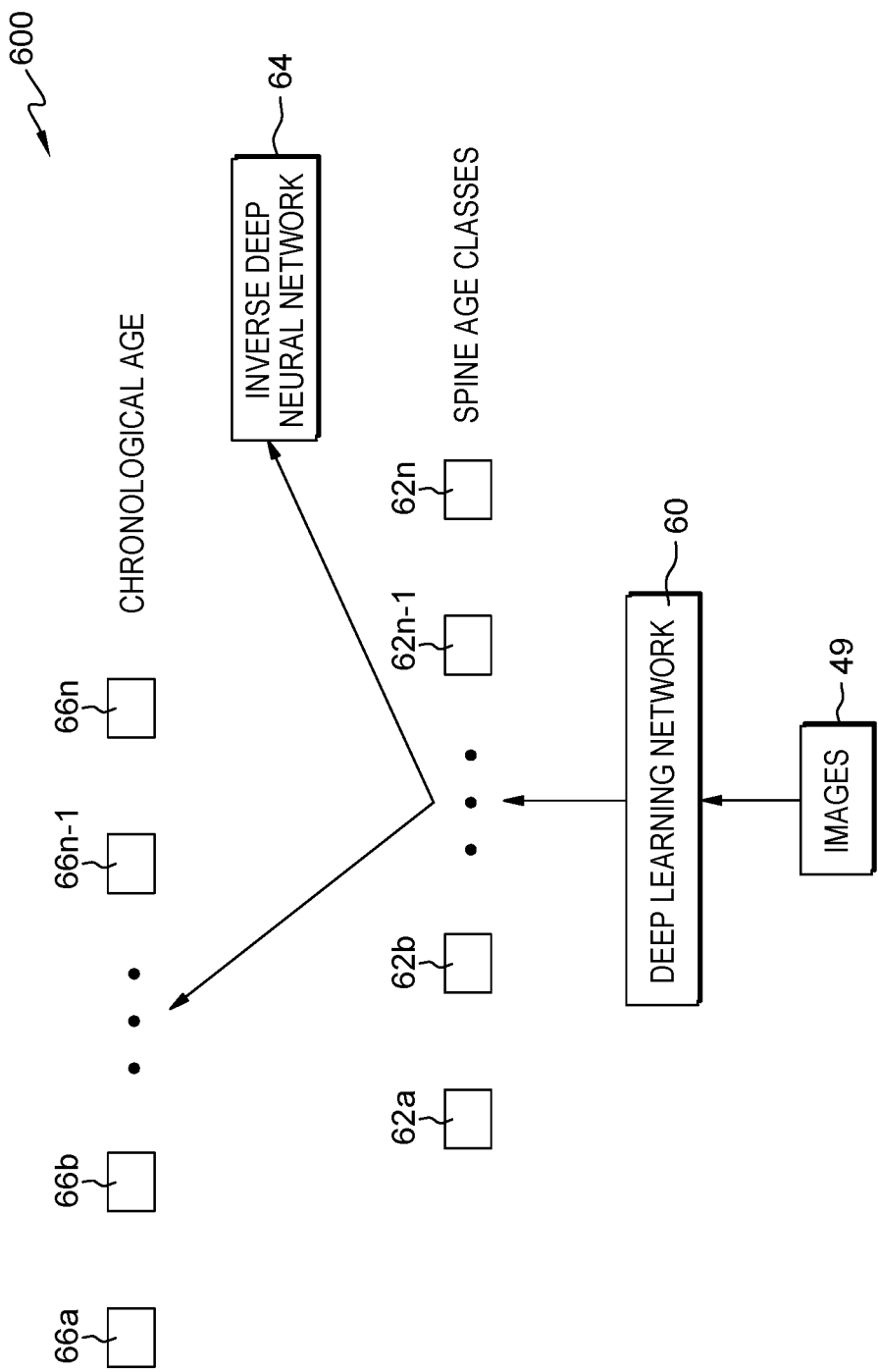

FIG. 6 is a schematic diagram of a method of unsupervised deep learning for training the apparent age program using an autoencoder, in accordance with at least one embodiment of the invention.

Figure 7:
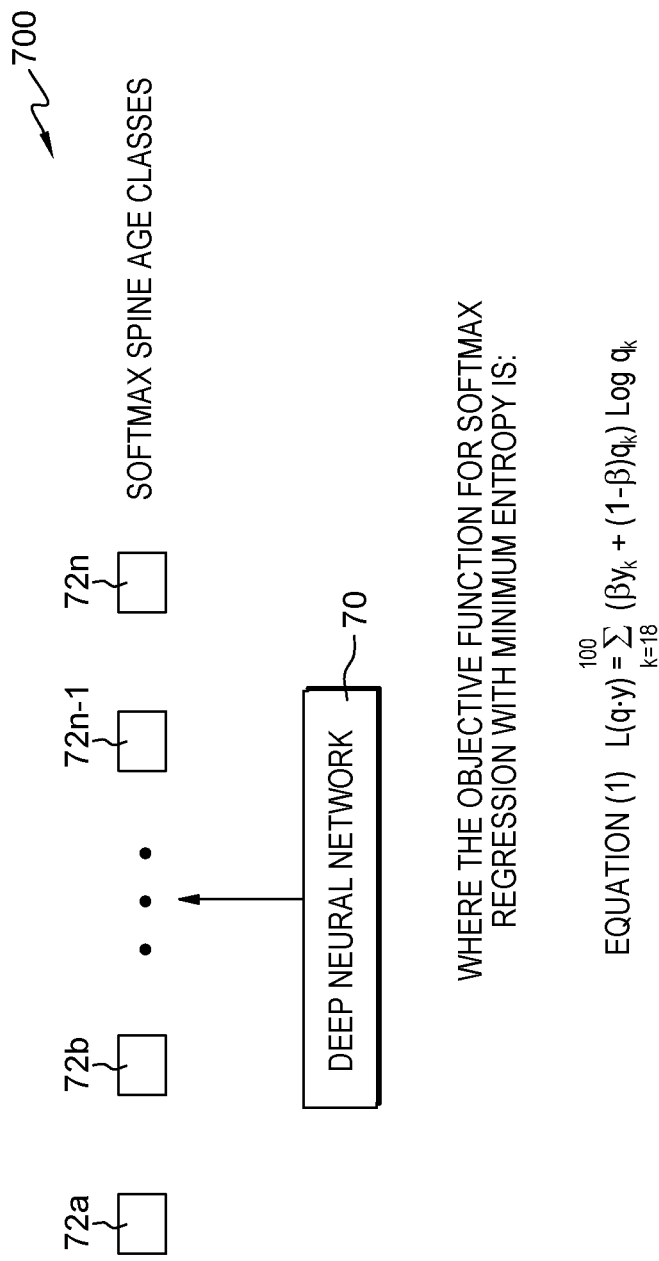

FIG. 7 is a schematic diagram of a method of unsupervised deep learning for training the apparent spine age program using soft labels, in accordance with at least one embodiment of the invention.

Figure 8:
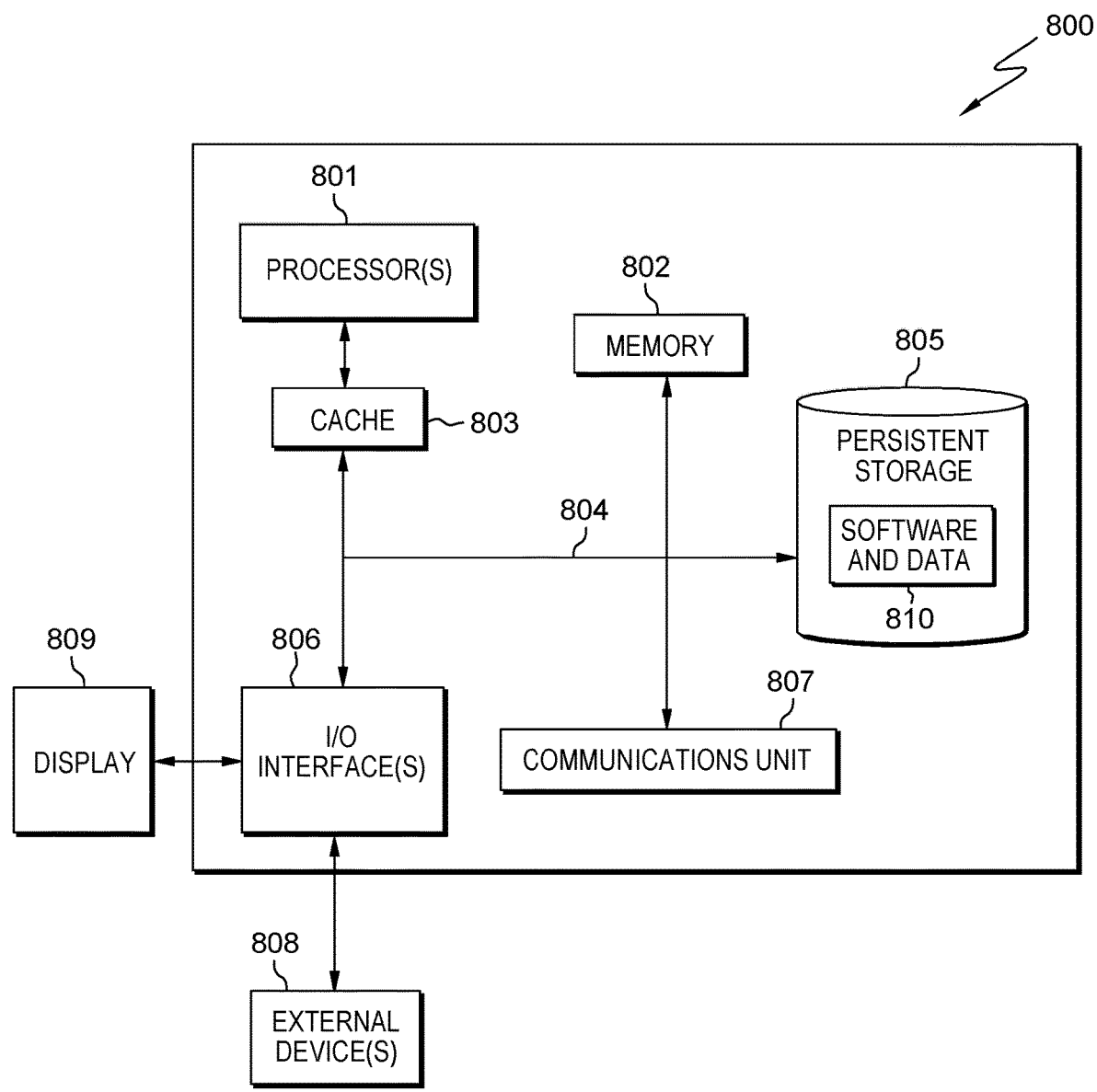

FIG. 8 is a block diagram depicting components of a computer system suitable for executing the apparent spine age program, in accordance with at least one embodiment of the present invention.

DETAILED DESCRIPTION

Embodiments of the present invention recognize that back pain is the most common symptom of spinal degeneration. Back pain can range from very mild or none to debilitating for individuals with spinal degeneration. Embodiments of the present invention recognize that the known risk factors for spinal degeneration include a family history of back pain or musculoskeletal disorders, excessive wear caused by heavy lifting or sports, poor posture during prolonged sitting, excess weight, or an acute injury to the spine. Embodiments of the present invention recognize that a number of preventative measures can be taken to reduce or prevent back pain including exercises, stretching, drugs, heat treatment, or spinal manipulation using physiotherapy.

Embodiments of the present invention recognize that a direct correlation of back pain to spinal degeneration or a direct correlation of back pain and spinal degeneration to risk factors associated with spinal degeneration does not exist. Embodiments of the present invention recognize that some people with one or more of the known risk factors for spinal degeneration may have little to no spine degeneration and little to no back pain while other people with none of the known risk factors for spine degeneration may have significant back pain and/or spine degeneration. Embodiments of the present invention recognize that methods of measuring osteoporosis of the vertebra or a disc of the spine exist. However, embodiments of the present invention recognize that a method to evaluate multiple factors associated with spine structure to determine spinal degeneration are not known.

Embodiments of the present invention recognize that a method to evaluate thousands of spine images to learn how to evaluate and apply an apparent spine age as a risk factor for spine degeneration would be advantageous for patients. Embodiments of the present invention recognize it would be desirable to identify individuals whose spine or a portion of the individual's spine, such as a vertebra or a disc, exhibits a high degree of spinal degeneration, beyond the amount of spine degeneration normally observed in individuals of a similar age. Embodiments of the present invention recognize that a program using trained machine learning algorithms, such as deep artificial learning algorithms, that considers multiple factors for identifying individuals whose functional or apparent spine age is significantly higher than their chronological age would be beneficial. The factors for identifying individuals with a functional spine age that is higher than the functional spine of other individuals of a similar chronological age are determined based on an analysis of a very large number of spinal images during unsupervised training of the machine learning algorithms. Embodiments of the present invention recognize an ability to detect individuals exhibiting greater than average spinal degeneration for their age group is advantageous in order to apply known preventative measures prior to developing further spinal degeneration.

Embodiments of the present invention provide a method, a computer program, and a computer system for an objective assessment of a spine, as well as, an objective assessment of individual vertebra and discs in the spine. Embodiments of the present invention provide a computer program using trained machine learning algorithms to determine an apparent age or functional age of an individual's spine as well as an apparent age of a portion of the spine, a single vertebra or a single disc. The computer program using artificial intelligence algorithms with deep learning networks trained using one of several unsupervised training approaches on a plurality of spinal images where the plurality of spinal images or scans ranges from hundreds to thousands of images for training. The program with a trained deep learning network can output a functional or an apparent age of the spine or a portion of the spine based, at least in part, on the unsupervised training of the deep learning network.

Embodiments of the present invention provide a computer program with machine learning algorithms that are trained without manual annotations or without the use of a ground truth. Embodiments of the present invention provide a computer program with machine learning algorithms, such as deep artificial intelligence algorithms, that are trained using one of several unsupervised training approaches. Embodiments of the present invention provide a method of providing an output, such as, an apparent spine age that identifies individuals whose apparent spine age is significantly higher than the individual's chronological age. In some embodiments, when the trained computer program identifies an apparent spine age of an individual that is greater than or significantly great than the individual's chronological age, a flag or a notation can be included in the analysis of the imaging or scan data even when the image or the scan is not specifically of the spine or a portion of the spine. Embodiments of the present invention provide a computer program that identifies to medical professionals, with a notation or a flag, spinal degradation in any computed tomography scan or magnetic resonance imaging scan of an individual that includes the spine or a portion of the spine. In this way, the individual, once notified by medical professionals of the spinal degeneration, can take preventive actions.

The present invention will now be described in detail with reference to the Figures.

Figure 1:
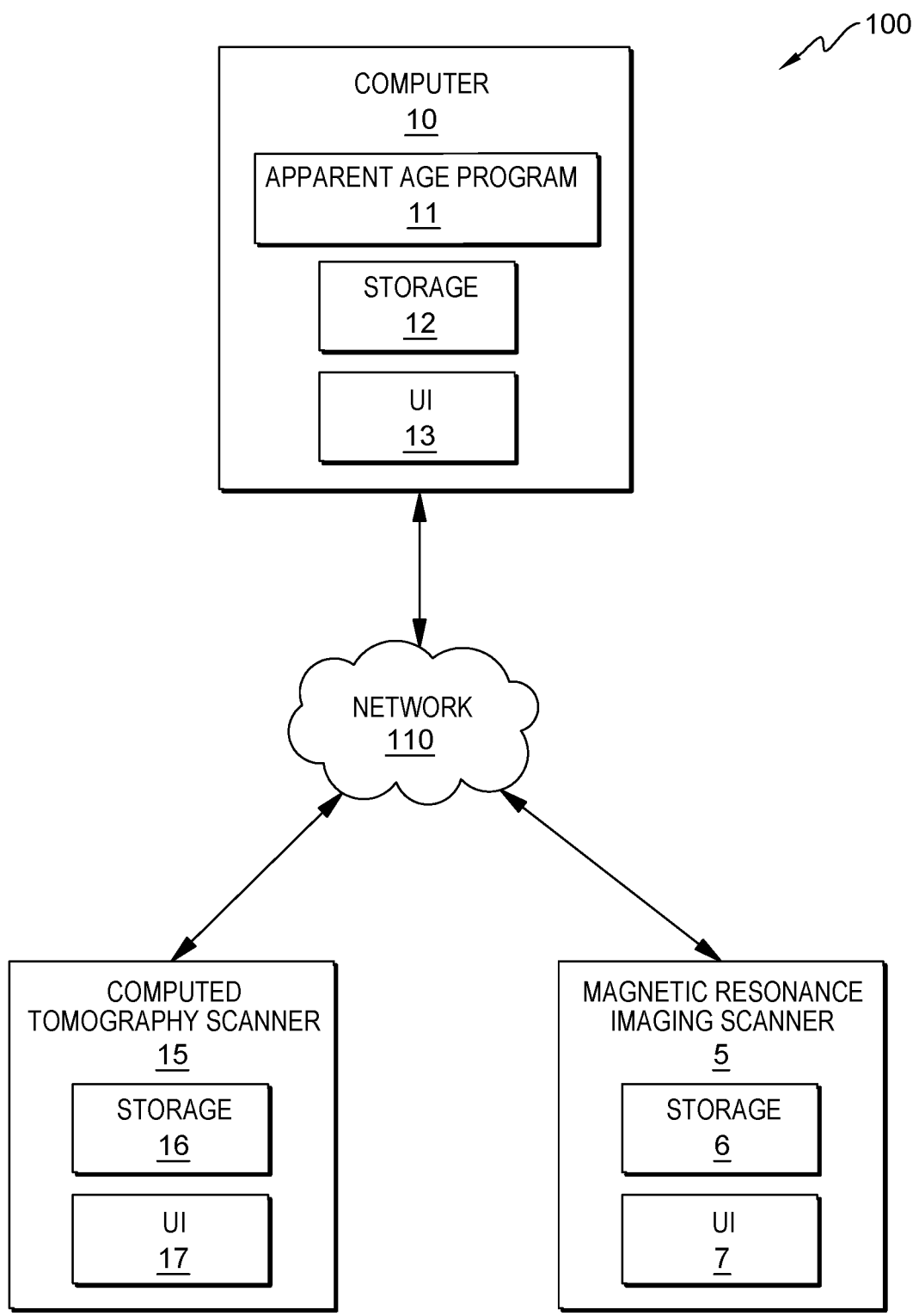
FIG. 1 depicts a functional block diagram of a computing environment suitable for operation of an apparent spine age program for a spine, a portion of the spine, a vertebra, or a spinal disc, in accordance with at least one embodiment of the invention.

FIG. 1 is a functional block diagram of a computing environment 100 suitable for operation of apparent spine age program 11 for a spine, a portion of the spine, a vertebra, or a spinal disc, in accordance with at least one embodiment of the invention. FIG. 1 provides only an illustration of one implementation and does not imply any limitations with regard to the environments in which different embodiments may be implemented. Implementation of embodiments of the invention may take a variety of forms, and exemplary implementation details are discussed subsequently with reference to the Figures. Many modifications to the depicted environment may be made by those skilled in the art without departing from the scope of the invention as recited by the claims.

Computing environment 100 includes computer 10, computed tomography (CT) scanner 15, and magnetic resonance imaging (MRI) scanner 5 connected over network 110. Network 110 can be, for example, a local area network (LAN), a wide area network (WAN), such as the Internet, a virtual local area network (VLAN), or any combination that can include wired, wireless, or optical connections. In general, network 110 can be any combination of connections and protocols that will support communications between computer 10, CT scanner 15, and MRI scanner 5 and any other computing devices not depicted in FIG. 1.

As depicted, computer 10 includes apparent spine age program 11, storage 12, and user interface (UI) 13. In various embodiments, computer 10 can be a desktop computer system, a mainframe computer, a laptop computer, a server, a tablet computer, or any other programmable electronic computing device capable of receiving, sending, and processing data, and communicating with features and functions of CT scanner 15 and MRI scanner 5 and other computing devices not shown within computing environment 100 via network 110. In some embodiments, computer 10 represents a computing system utilizing clustered computers and components (e.g., database server computers, application server computers, etc.) that act as a single pool of seamless resources when accessed within distributed data processing environment 100, such as, a cloud computing environment. Computer 10 may include internal and external hardware components, as depicted in more detail and described in FIG. 8.

Apparent spine age program 11 is depicted as operating on computer 10. In various embodiments, once trained, apparent spine age program 11 provides an evaluation of an apparent age of one of a person's spine or a portion of a person's spine based, at least in part, on received or retrieved data from one of CT scanner 15 or MRI scanner 5. In various embodiments, apparent spine age program 11 receives or retrieves a large number of spinal images from one or more of CT scanner 15, MRI scanner 5, or another imaging device for training to determine an apparent spinal age of a subject.

In various embodiments, once trained, apparent spine age program 11 receives or retrieves one of CT scan data, CT volume data, MRI scan data, or X-ray data of a spine, a portion of a spine, a vertebra, or a disc to determine an apparent age of the spine, an apparent age of the portion of the spine, an apparent age of the vertebra, or an apparent age of the disc associated with the respective image data. In some cases, apparent spine age program 11 may receive CT scan data or MRI scan data captured for the evaluation of another organ or another portion of a patient's body, such as the digestive track, which also includes the spine or a portion of the spine that may be used for training of the machine learning algorithm. In other cases, when a trained apparent spine age program 11 receives CT or MRI scans of other organs or body parts that include a patient's spine or a portion of the patient's spine then, apparent spine age program 11 adds a notation of a determined apparent spine age and/or a notation of one or more of an apparent spine age, an apparent vertebra age, or an apparent spinal disc age that is significantly older than the patient's chronological age. In these embodiments, apparent spine age program 11 includes s pre-set number of years, such as, five years older, as a significant difference between the apparent spine age and the patient's chronological age. When the pre-set number of years is exceeded, apparent spine age program 11 adds a flag or a notation of significant spine, vertebra, or disc degeneration to the radiologist.

In various embodiments, apparent spine age program 11 pre-processes image data, such as a CT scan, a CT volume, or an MRI scan. The pre-processing can extract subvolumes containing the spine or a portion of the spine (e.g., three vertebra and two disc or a vertebra). For example, a CT volume can be pre-processed to extract subvolumes of a spine, of a portion of the spine, such as three vertebrae and two discs, a vertebra, or a disc. The extracted volume or subvolumes can be a two-dimensional section or a three-dimensional section of the spine or a portion of the spine (e.g., a vertebra, a disc, etc.). Pre-processing of received imaging data can be done for both the training of the deep learning neural network and for an evaluation of a specific patient's imaging data by the trained apparent spine age program 11. In one embodiment, apparent spine age program 11 resides on CT scanner 15. In this embodiment, once trained, apparent spine age program 11 retrieves CT scan data from storage (not depicted) in CT scanner 15 and determines one of an apparent spinal age, an apparent vertebra age, or an apparent disc age. In another embodiment, apparent spine age program 11 resides on MRI scanner 5. Apparent spine age program 11 may receive and send data to and from CT scanner 15, MRI scanner 5, and other computer devices not depicted within computing environment 100 using network 110.

In various embodiments, apparent spine age program 11 training occurs using a very large number of received or retrieved CT scans, CT volumes, MRI volumes, or X-rays associated with human spines or a portion of human spines. FIGS. 5-7 depict a number of approaches to training one or more deep learning networks in apparent spine age program 11 using unsupervised training. In some embodiments, the deep learning algorithms or deep learning networks in apparent spine age program 11 are one of a convolutional neural network or a recurrent neural network. However, the deep learning networks in apparent spine age program 11 are not limited to one of a convolutional neural network or a recurrent neural network.

Apparent spine age program 11 may send an output, such as, an apparent spine age, an apparent disc age, an apparent age of a portion of the spine, or an apparent vertebra age, determined by the trained apparent spine age program 11 from an evaluation of a received CT scan or MRI scan to storage 12 in computer 10. In various embodiments, apparent spine age program 11, when trained, displays the apparent age of one of the patient's spine, a vertebra, or a disc captured in the CT scan data or MRI scan data in UI 13. In some cases, apparent spine age program 11 receives a user input on UI 13 to send an output or an apparent spine age to a computing device of a patient or a computing device of a medical professional. In some embodiments, apparent spine age program 11 provides a notation in the output of apparent spine age program 11 or adds meta data associated with the received spine image data indicating to a medical professional when significant spinal degeneration is determined.

CT scanner 15 is a computing device capable of performing a CT scan (also known as a computed axial tomography or CAT scan). CT scanner 15 uses known medical imaging techniques that utilize computer-processed combinations of multiple X-ray measurements taken from different angles to produce tomographic (cross-sectional) images or virtual slices of a body. As depicted, CT scanner 15 includes storage 16 and UI 17. In one embodiment, CT scanner 15 includes the computing processors and computing devices capable of executing apparent spine age program 11. In various embodiments, CT scanner 15 captures images of a patient's spine with one or more vertebra and disc. In various embodiments, CT scanner 15 receives a user input on UI 17 to send one or more spinal images to computer 10. CT scanner 15 may store captured spinal images in storage 16. While depicted as a single CT scanner 15, more than one CT scanner 15 can provide spinal image data to apparent spine age program 11 in computer 10 and other computing devices not depicted in computer environment 100 over network 110.

MRI scanner 5 uses strong magnetic fields, magnetic field gradients, and radio waves to generate images of the organs in the body using known technology. In various embodiments, MRI scanner 5 generates MRI images of a patient's spine. As depicted, MRI scanner 5 includes storage 6 and UI 7. In one embodiment, MRI scanner 5 includes the computing processors and computing devices capable of executing apparent spine age program 11. In an embodiment, MRI scanner 5 captures MRI images of the patient's spine, sections of the patient's spine, a vertebra, or a disc. In various embodiments, MRI scanner 5 receives a user input on UI 7 to send one or more spinal images to computer 10. MRI scanner 5 may store captured spinal images in storage 6. While depicted as a single MRI scanner 5, more than one MRI scanner 5 can provide spinal image data to apparent spine age program 11 in computer 10 and other computing devices not depicted in computer environment 100 over network 110.

Figure 2:
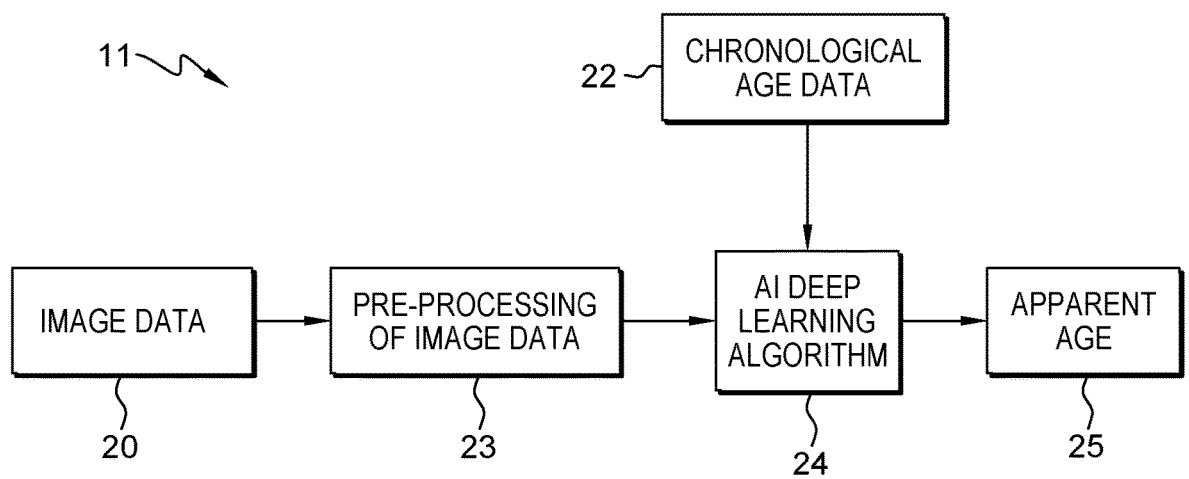
FIG. 2 is an example of a schematic diagram of a method using a trained apparent age program to determine an apparent spinal age of a spine in a patient, in accordance with at least one embodiment of the invention.

FIG. 2 is an example of a schematic diagram of a method to determine an apparent spinal age of a patient using apparent spine age program 11, in accordance with at least one embodiment of the invention. As depicted, FIG. 2 includes image data 20, chronological age data 22, pre-processing 23, artificial intelligence (AI) deep learning 24, and apparent spine age 25, where a trained apparent spine age program 11 processes image data 20 and receives chronological age data 22 of the patient which is processed using AI deep learning 24 to output an apparent spine age of the patient's spine.

As depicted in FIG. 2, apparent spine age program 11, which has been trained using many spinal images using one or more of the approaches discussed in detail later with respect to FIGS. 5-7, receives image data 20. In various embodiments, image data 20 is from an image from a patient. The image data 20 can be one of the following: an image of a complete spine, a portion of a spine, a vertebra, or a disc. Image data 20 can be input into a trained apparent age program 11 from one of CT scanner 15 or MRI scanner 5 (depicted in FIG. 1), or other imaging device (e.g., an X-ray machine, etc.). In some embodiments, image data 20 is one of a CT volume or an MRI scan. In some cases, apparent age program 11 retrieves the image data 20 from one of storage 13, storage 16, storage 6 or another storage location not depicted in FIG. 1. As known to one skilled in the art, volume rendering is a type of data visualization technique which creates a three-dimensional representation of data. CT scan data and MRI scan data of the spine can be visualized with volume rendering to provide three-dimensional images of the spine or sections of the spine. In other embodiments, image data 20 is one of a two-dimensional CT image, an MRI image, an X-ray, or other image of the patient's spine.

Upon receiving spinal image data 20, apparent spine age program 11 pre-processes image data 20 in pre-processing 23. In various, embodiments, during pre-processing 23, apparent spine age program 11 extracts one or more sub-volumes from the CT volume. For example, during pre-processing 23, the trained apparent spine age program 11 may extract one or more subvolumes from the CT volume containing the spine, a portion of the spine, a single vertebra or a single disc. The CT volumes or subvolumes can be a three-dimensional cross-section of the spine or a portion of the spine, such as, three vertebra and two discs, a vertebra or a disc. In some embodiments, two-dimensional sections of the spine, a vertebra, or a disc are extracted by apparent spine age program 11.

In various embodiments, the extraction of CT subvolumes containing portions of the spine by apparent spine age program 11 is done by determining a center of a vertebra, by determining the center of each vertebral bodies, or by determining a another landmark in each of the vertebra, such as, the center of the spinal cord, and then, extracting a volume of the CT scan. For example, apparent spine age program 11 extracts the portion of the CT image that contains exactly one vertebra or a given vertebrae with a pre-determined number of adjacent vertebrae. In some cases, apparent spine age program 11 uses pre-processing 23 to extract a CT subvolume associated with each vertebra. In this case, the number of CT subvolumes would equal the number of vertebrae in a human spine. In this example, apparent spine age program 11 could execute sequentially on each vertebra in the patient's spine to produce an apparent spine age associated with the complete spine of the patient. A similar approach could be applied by apparent spine age program 11 for pre-processing 23 when image data 20 is MRI scan data.

In some embodiments, pre-processing 23 by apparent spine age program 11 includes vertebrae labelling (e.g., C1, C2, and so on). In various embodiments, when pre-processing 23 of image data 20 is complete, then the CT or MRI image data consists of a series of two-dimensional sections or three-dimensional sections (e.g., subvolumes) of the entire spine or of a portion of the spine (e.g., vertebrae C1-C7). In some cases, when spinal surgery or spine augmentation has occurred (e.g., kyphoplasty or vertebroplasty) then, the sections of the spine affected by the surgery and/or therapeutic hardware are excluded from spinal age analysis by apparent spine age program 11. In some embodiments, the pre-processing of image data 20 in block 23, the data from pre-processing of image data 20 that occurs in block 23 is analyzed by the trained AI deep learning algorithm 24 in apparent spine age program 11 as a single volume (e.g., a vertebra or a complete spine). In other embodiments, the pre-processed data is analyzed using AI deep learning algorithm 24 as a sequence of CT sub-volumes or as a series of two-dimensional slices or sections of the patient's spine.

After completion of pre-processing of image data 20 in block 23, apparent spine age program 11 executes a trained machine learning algorithm that is depicted as AI deep learning algorithm 24 using chronological age data 22 of the patient that is input into apparent spine age program 11 by a user. A detailed discussion of some of the approaches to unsupervised deep learning for possible methods to model or estimate an apparent spine age without a ground truth (e.g., without knowing the apparent spinal age) are discussed in detail with regard to FIGS. 5-7. Upon receiving chronological age data 22, the trained AI deep learning algorithm 24, executes as an apparent age prediction model within apparent spine age program 11. Using AI deep learning algorithm, apparent spine age program 11 outputs apparent age 25 of the patient's spine or apparent age 25 of a disc or vertebra of the patient.

As previously discussed, apparent age 25 of the patient is a functional or apparent age of the spine or a portion of the patient's spine determined from image data 20 based, at least in part, on the training of AI deep learning algorithm 24 using vast amounts of image data of spines. In various embodiments, apparent age 25 reflects the amount of spinal degeneration commonly associated with a specific chronological age as determined from hundreds or thousands of spine imaging data during training of apparent spine age program 11. For example, for a patient, chronological age data 22 indicates that received chronological age of the patient is 51 years however, the analysis by apparent spine age program 11 using at least image data 20 and the trained AI deep learning algorithm 24 indicates that the structure of the patient's spine from image data 20 would typically be associated with a 65 year old person.

In various embodiments, when apparent age 25 is greater by a pre-determined amount pre-set in apparent spine age program 11 then, apparent spine age program 11 will add a notation or a comment to the output and/or as a notation or metadata associated with image data 20 for the radiologist or another medical professional. For example, when apparent age 25 output by apparent spine age program 11 is more than five years greater than the patient's chronological age then, apparent spine age program 11 adds a notation to the output and to image data 20 of excessive spinal degeneration. In this case, a medical professional, upon viewing the output of apparent spine age program 11 with the notation of excessive spine degeneration, may consider initiating preventive measures with the patient, such as, exercises or stretches designed to slow or reverse the spinal degeneration.

Figure 3A:
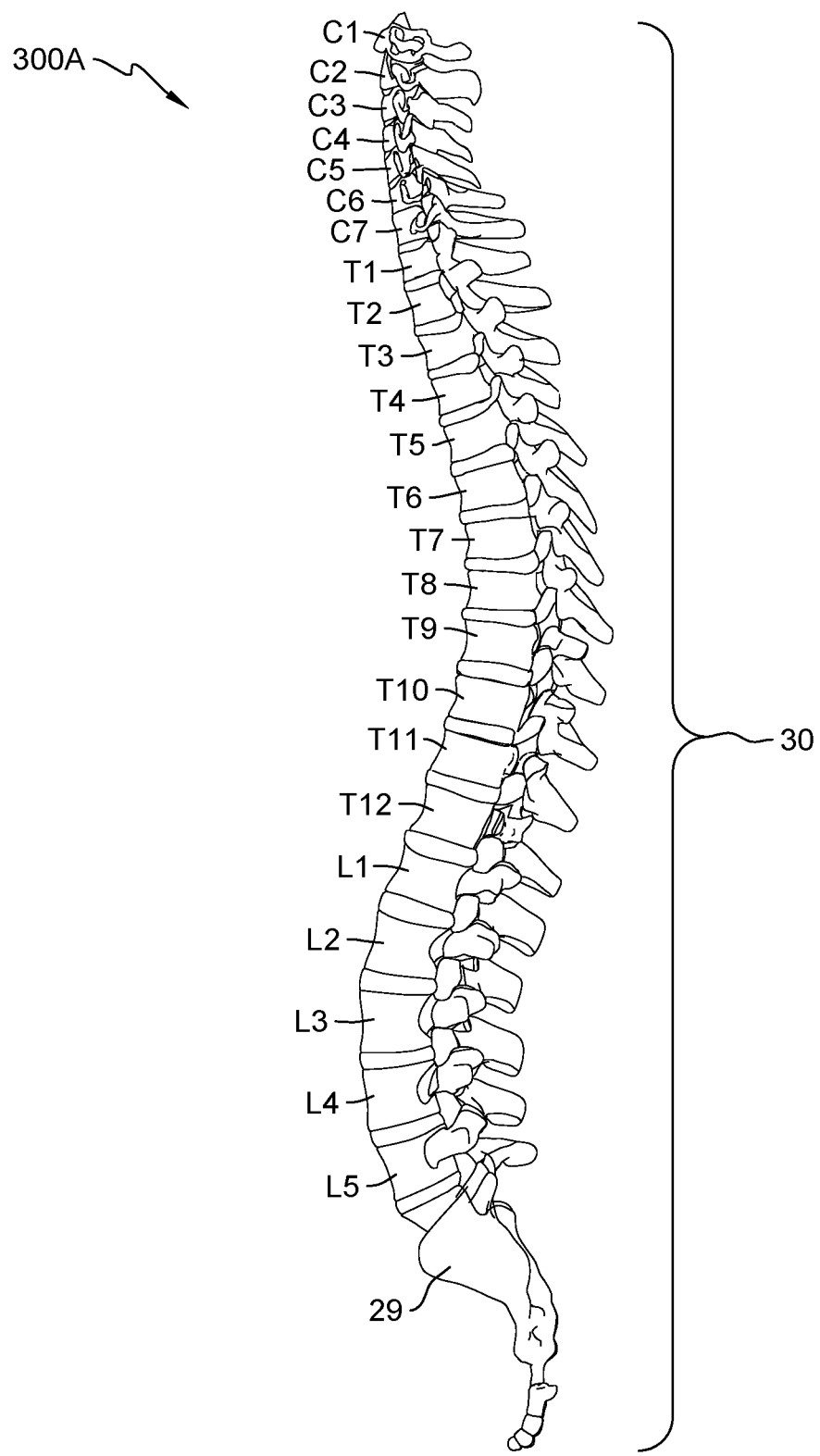
FIG. 3A is an illustration of a human spine with vertebrae labelling, in accordance with at least one embodiment of the invention.

FIG. 3A is an example of illustration 300A of human spine 30 with vertebrae labelling C1-L5 as captured in a scan of a patient, in accordance with at least one embodiment of the invention. As depicted, FIG. 3A includes spine 30 composed of vertebrae C1-C7, T1-T12, L1-L5, and fused sacrum and coccyx 29 as may be captured by one of CT scanner 15 or MRI scanner 5 depicted in FIG. 1. As known to one skilled in the art, the vertebrae of the spine are numbered and divided into regions, such as the cervical region that is composed of C1-C7 vertebrae, the thoracic region composed of T1-T12 vertebrae, the lumbar region composed of L1-L5 vertebrae, and sacrum and coccyx 29 that are fused together (from top to bottom of spine 30). The image of spine 30 can be retrieved from CT scanner 15, MRI scanner 5, storage 13, storage 16, storage 6, or another storage location or database not depicted in FIG. 1.

In various embodiments, a CT or MRI scan of a patient provides a complete or full image of spine 30. In other embodiments, a CT or MRI scan of a patient provides an image of a portion of spine 30. In same embodiments, during pre-processing of the spine image data, apparent spine age program 11 determines a centerline through spine 30 (not depicted in FIG. 3A) into to analyze spine image data and/or determine subvolumes of the CT scan or MRI scan. As previously discussed, apparent spine age program 11 in computer 10 of FIG. 1 may determine an apparent spine age of spine 30 or a portion of spine 30 (e.g., one or more of vertebra C1-L6 or any of the discs between adjacent vertebra of vertebrae C1-L6) based, at least in part, on unsupervised training of a machine learning algorithm in apparent spine age program 11 using a training set of retrieved spine images (e.g., greater than a thousand images).

Figure 3B:
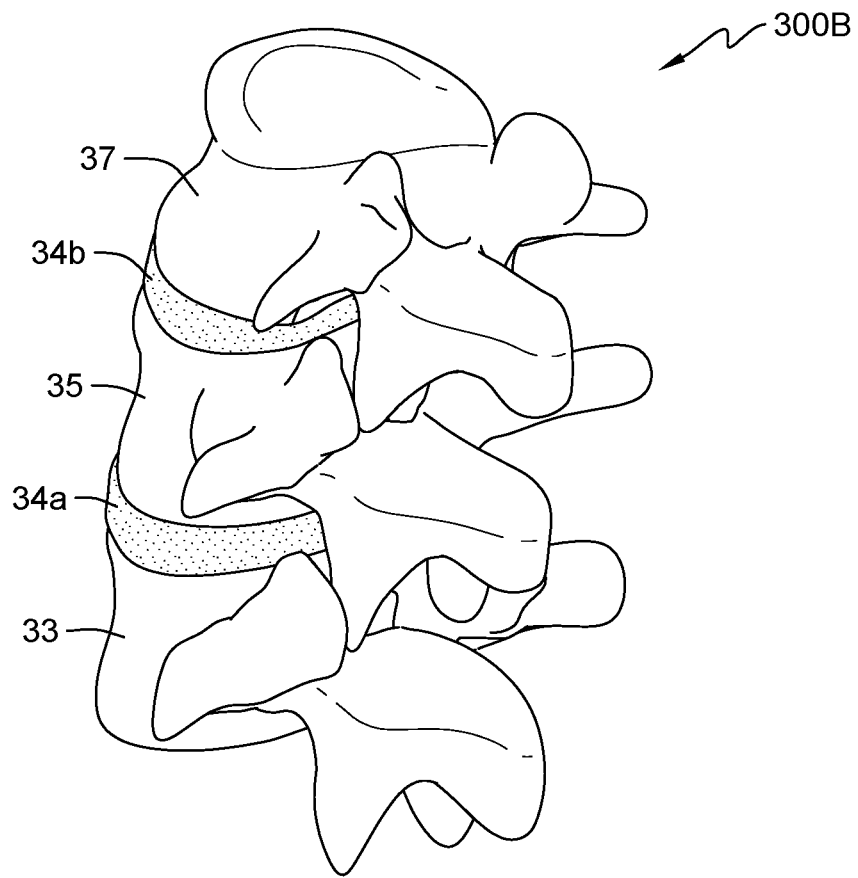
FIG. 3B is an illustration of a three-dimensional section of several vertebra and disc, in accordance with at least one embodiment of the invention.

FIG. 3B is illustration 300B of a three-dimensional section of vertebra 33, 35, and 37 with discs 34a and 34b, in accordance with at least one embodiment of the invention. Illustration 300B is one example of a portion of a CT scan or a portion of CT volume of a portion of a spine that is composed of vertebra 33, 35, and 37 with disc 34a and 34b between vertebra 33 and 35 and vertebra 35 and vertebra 37 respectively. For example, in some cases, the section of spine 30 depicted in illustration 300B may be a subvolume or a partial volume of a CT scan volume captured by CT scanner 15. In other examples, illustration 300B may be an MRI scan or portion of an MRI scan of spine 30 in FIG. 1 that is used by apparent spine age program 11 to determine an apparent age of the spine, an apparent age of a portion of the spine or for training of apparent spine age program 11. Vertebra 33, 35, and 37 may be any vertebra depicted in spine 30 in FIG. 1. In some embodiments, only one of vertebra 33, 35, or 37 is extracted by apparent spine age program 11. While depicted as a three-dimensional section of spine 30 in FIG. 3A, in other embodiments, vertebra 33, 34, 37, and disc 34a and 34b could be two-dimensional sections of spine 30. In other examples, vertebra 35 with disc 34a and 34b may be extracted and used by apparent spine age program 11. In some embodiments, apparent spine age program 11 extracts disc 34a for training of apparent spine age program 11 or for determining disc 34a apparent age after training of apparent spine age program 11.

Figure 3C:
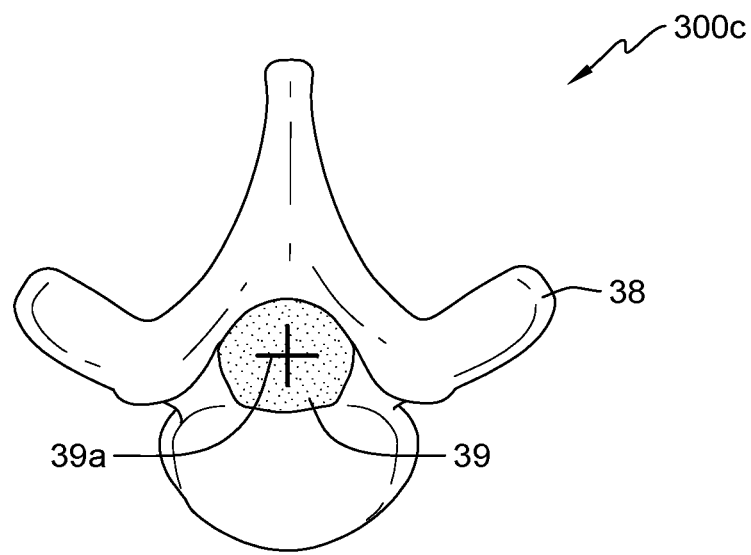

FIG. 3C is illustration 300C of a two-dimensional section of vertebra 38, in accordance with at least one embodiment of the invention. As depicted, FIG. 3C includes vertebra 38, spinal cord 39, and center 39a. In some cases, center 39a can be a center of vertebra 38, a center of spinal cord 39, or another landmark for apparent spine age program 11 to use in pre-processing of the retrieved image data or scan data. In other embodiments, a two-dimensional section of a CT scan, an MRI scan, or an X-ray of a disc, such as, disc 34a in FIG. 3B, may be extracted or used by apparent spine age program 11 to determine an apparent spine age.

FIG. 4 is a flow chart diagram depicting operational steps 400 for training apparent spine age program 11, in accordance with at least one embodiment of the invention. As depicted, FIG. 4 includes apparent spine age program 11 receiving spine imaging data, apparent spine age program 11 pre-processing spine imaging data, and training machine learning algorithms in apparent spine age program 11 with unsupervised deep learning using one or more of an additional softmax layer, an autoencoder, and soft labelling in apparent spine age program 11. FIG. 4 depicts an example of training apparent spine age program 11 with vast amounts of spine imaging data and using at least one of three methods of unsupervised deep learning (e.g., using an additional softmax layer, using an autoencoder, or using soft labelling).

In step 402, apparent spine age program 11 receives spine imaging data. In some embodiments, apparent spine age program 11 receives a user input to retrieve spine imaging data from one or more of storage 13, storage 17, storage 7, or another storage location or database not depicted in FIG. 1. As previously discussed with reference to FIG. 2, the received or retrieved spine imaging data can be one or more of a CT scan, a CT volume, an MRI scan, an X-ray, a positron emission tomography (PET) scan using a dye containing radioactive tracers, or other suitable images of the spine or a portion of the spine from more than one subject or hundreds or more different subjects (i.e., from many different subjects). In some cases, the spine imaging data may be incidental spinal images captured during an evaluation of other organs or the spinal imaging data can spinal images captured for spine degeneration analysis. In various embodiments, apparent spine age program 11 receives or retrieves a large number of spine images captured by one of CT scanner 15 or MRI scanner 5 depicted in FIG. 1. For example, several thousand spine images or several hundred spine images from different subjects can be received or retrieved for training of the deep learning AI algorithm in apparent spine age program 11.

In step 404, apparent spine age program 11 pre-processes spine imaging data. The pre-processing of spine imaging data occurs as previously discussed with regard FIG. 2. For example, for a given received or retrieved CT volume, apparent spine age program 11 may extract a subvolume of the received CT volume. The subvolume of the CT volume may contain the full spine, a portion of the spine (e.g., 3 vertebrae and associated disc), a specific vertebra, or a specific disc. Similarly, apparent spine age program 11 may extract a two-dimensional cross-section of a vertebra (depicted in FIG. 3C), a disc, a portion of the spine, or the spine or a three-dimensional section of the spine or a portion of the spine (e.g., depicted in FIGS. 3A and 3B). In some embodiments, apparent spine age program 11 extracts a portion of a spine, a vertebra, a disc, or a complete spine from an MRI scans received by apparent spine age program 11. The extraction of the spine or a vertebra from a CT image, CT volume, an MRI scan, or an X-ray may utilize a method of determining one of center of a specific spinal body, such as a center of a vertebra, a spinal cord (depicted in FIG. 3C), or a disc. In other cases, the distance from a landmark or a specified area around a specified landmark may be used by apparent spine age program 11 to extract the volume or cross-section associated with a specified spine element or a complete spine. In another method, apparent spine age program 11 determines a centerline of the spine and determines a volume adjacent to the centerline. The volume adjacent to the centerline can contain two-dimensional cross-sections or three-dimensional cross-sections perpendicular to the centerline of one or more vertebra or discs. In some cases, pre-processing would include labelling each vertebra in each spine image as depicted in FIG. 3A.

In step 406, apparent spine age program 11 trains the machine learning algorithm using unsupervised deep learning. Ground truth (GT) labels are used in supervised learning approaches. However, creating a ground truth for an apparent spine age is impractical (e.g., one does not know the apparent spine age in advance). For example, a level of backpain is subjective and does not correlate well with a level of spine degeneration. Spine degeneration assessments from different radiologists are subjective assessments and may vary from radiologist to radiologist and would require many assessments of a spine image to be robust. For these reasons, an unsupervised deep learning approach can be used in training apparent spine age program 11 instead of a traditional supervised learning approach using one or more GT labels.

In various embodiments, in apparent spine age program 11, in order to overcome an inability to provide a good GT, a latent variable, $\hat{y}$, indicates apparent spine age and a chronological age, y, is an observed variable that is a random variable derived from some unknown distribution $p(y|\hat{y})$. Although the distribution $p(y|\hat{y})$ is unknown, an assumption of a known functional form can be made (e.g., Gaussian distribution, a gamma distribution, etc.). In various embodiments, a Gaussian distribution is assumed for the distribution $p(y|\hat{y})$. In some embodiments, apparent spine age program 11 also uses a gamma distribution to account for possible asymmetry in the $p(y|\hat{y})$ distribution. In some cases, the distribution $p(y|\hat{y})$ is dependent on some latent variable, for example, sigma. For example, when a Gaussian distribution is assumed then, sigma is an unknown standard deviation of this distribution. In general, sigma can be a function of apparent spine age $\hat{y}$.

In various embodiments, the unsupervised training of the machine learning or AI algorithm in step 406 occurs using one or more the approaches discussed with respect to step 408, step 410, or step 412. In general, different approaches can be combined or ensembled to provide more accurate results.

In step 408, in one approach, apparent spine age program 11 trains the machine learning algorithm using unsupervised deep learning with an additional softmax layer. During training, when the model in apparent spine age program 11 is determined with a deep learning neural network with a densely connected softmax layer then, another softmax layer is added on top of the last densely connected softmax layer.

As known to one skilled in the art, a softmax layer or a softmax function, which may also be known as a normalized exponential function, is a generalization of the logical function to multiple dimensions and may be used in multinomial logistical regression. In many cases, the softmax function or the softmax layer can be used as the last activation function of a neural network to normalize the output of the neural network to a probability distribution over predicted output classes. Often, the softmax layer can be implemented through a neural network layer just before the output layer.

In various embodiments, apparent spine age program 11 uses the deep learning neural network with the additional softmax layer to model p (y, ŷ). During training, the deep neural network or deep learning network in apparent spine age program 11 learns the values of the weights of the deep learning network and the parameters of p(y|ŷ) distribution (e.g., like sigma) can be learned from the data providing the chronological age of patients as a target variable. FIG. 5 depicts a schematic of apparent spine age program 11 with the deep learning neural network using an additional softmax layer on top of the last densely connected softmax layer. Note that although apparent age is a continuous variable, apparent age is made discreet and a classification approach is used.

In step 410, in another approach, apparent spine age program 11 trains the machine learning algorithm using unsupervised deep learning using an autoencoder. In some cases, the approach discussed above relative to step 408 when the objective function is maximized for ŷ=y then, the deep learning network in apparent spine age program 11 can overfit the p(y|ŷ) distribution making it difficult to effectively train the deep learning network. To correct for possible overfitting, an autoencoder can be used to provide consistency and an estimate of the latent variable, ŷ. In this case, consistency can be achieved when similar spine images output similar values for ŷ (e.g., similar apparent spine ages). As known to one skilled in the art, an autoencoder is a type of artificial neural network used to learn efficient data coding in an unsupervised manner where the aim of an autoencoder is to learn a representation or encoding for a set of data, typically for dimensionality reduction, by training the network to ignore signal "noise". Autoencoder can be considered unsupervised or self-supervised because they generate their own labels from the training data. An example of a schematic diagram of apparent spine age program 11 training the machine learning algorithm using an autoencoder for the unsupervised deep learning is depicted in FIG. 6.

In step 412, in yet another approach, apparent spine age program 11 trains the machine learning algorithm using unsupervised deep learning using soft labelling. In this embodiment, soft labelling is used with a softmax regression with minimum entropy conditions. Minimum entropy encourages estimations which are precise. A soft label is a label which has a probability attached to it. For example, a probability, such as 0.1, 0.3, or 0.5, (e.g., instead of a 0 or a 1) can be determined for a soft label. In some cases, soft labels may provide a model or network in apparent spine age program 11 with a more accurate description of the actual information about each sample or spine image. FIG. 7 with equation (1) depicts schematic diagram 700 with one example of training the machine learning algorithm using unsupervised deep learning using soft labels. The details of step 412 are discussed in more detail later with respect to FIG. 7. In this case, the deep learning neural network does not use the explicit form of p(y|ŷ) distribution (e.g., where the p(y|ŷ) distribution is assumed to be Gaussian). In this case, the deep learning network in apparent spine age program 11 extracts non-parametric form of p(y|ŷ) directly from the training data.

Once the training of the machine learning algorithm in apparent spine age program 11 occurs using one of the approaches in steps 408, 410 or 412 as discussed in more detail later with regard to FIGS. 5, 6, and 7 respectively, then, is some cases, a validation of apparent spine age program 11 can be performed using one or more of various methods.

In one method, the validation of the training of apparent spine age program 11 can be done indirectly when no ground truth labels are available (e.g., as discussed in step 408). For example, a set of unlabeled spine images from a high-risk population (e.g., people with previous back injuries, people with a family history of musculoskeletal disorders, people with excessive wear of the spine due to sports or heavy lifting in jobs, etc.) to test if apparent spine age program 11 output of apparent spine ages reflect the high-risk of this population. In this case, a test data set of approximately one thousand cases or patients with a known chronological age and from this data set, a histogram is created that approximates the distribution p(y) associated with chronological ages. Next, using the trained apparent spine age program 11, determine a histogram or distribution p(ŷ) of the apparent spine age for the test data set. For example, using the equation $P_{est}(y)=\int P(\hat{y})p(y|\hat{y})$ a test of the hypothesis that $P_{est}(y)$ equals $P(\hat{y})$ can occur.

Another method of validating the training of apparent spine age program 11 could be done using ground truth labels created by human experts, such as, doctors or radiologists. In this method, the human experts annotate the test data set. The experts can provide an apparent age based on their experience and use this data to validate the model (e.g., apparent spine age program 11). For example, another test data set of approximately one hundred cases or spine images are each examined by an experienced radiologists who estimates the apparent spine age based at least in part, on viewing one or more of axial images, CT volume renderings of the spine, and/or other spine images or data. A comparison of the output of an apparent spine age from trained apparent spine age program 11 and the experienced radiologist apparent age estimate of spine images and data can be done to determine if the output of an apparent spine age is the same or approximately the same as the radiologist determined apparent spine age in order to validate the training of apparent spine age program 11.

FIG. 5 is schematic diagram 500 of one method of unsupervised deep learning for training the apparent spine age program using additional softmax layer 54a-54n in step 408 of FIG. 4, in accordance with at least one embodiment of the invention. FIG. 5 provides schematic diagram 500 depicting additional details of the method of training deep learning network 50 using unsupervised training with reference to step 408 of FIG. 4. As depicted, FIG. 5 includes images 49, deep learning network 50, softmax spine age classes 52a-52n, and additional softmax layer 54a-54n for softmax chronological age y in apparent spine age program 11. Schematic diagram 500 is of a feed-forward network with the additional softmax layer 54a-54n for the latent variable, ŷ, in softmax spine age classes for ŷ. Images 49 includes image data, such as, spine image data, vertebra image data, or disc image data is received by deep learning network 50 for training in apparent spine age program 11. For training, images 49 can be hundreds or thousands of images 49 from hundreds or thousands of different subjects.

After determining softmax spine age classes ŷ, the additional softmax layer 54*a*-54*n* models the distribution p(y|ŷ), the unknown distribution.

Another variation of this approach uses noisy labels. In this embodiment, the latent variable is assumed along with the model in apparent spine age program 11, then supervised training with noisy labels is performed. Any one of the known methods to apply noisy labels can be used in this example.

FIG. 6 is illustration of a schematic diagram 600 of a method of unsupervised deep learning for training apparent spine age program 11 using an autoencoder, in accordance with at least one embodiment of the invention. FIG. 6 provides a schematic diagram depicting additional details of the method of training deep learning network 60 as the machine learning algorithm using unsupervised training with reference to step 410 of FIG. 4. As depicted, FIG. 6 includes images 49, deep learning network 60, spine age classes 62*a*-62*n*, where spine age classes 62*a*-62*b* are apparent spine age classes, inverse deep learning network 64, and chronological age 66*a*-66*n* in apparent spine age program 11, where deep learning network 60 receives image data (e.g., complete spine, a portion of a spine, a vertebra, or a disc) from CT scanner 15, MRI scanner 5, (depicted in FIG. 1) or another source and inverse deep learning neural network 60 outputs images.

In the method discussed above with respect to FIG. 5, when the objective function in equation (1) is maximized for ŷ=y then, deep learning network 60 may overfit the objective function making training of deep learning network difficult. In various embodiments, to account for overfitting, an autoencoder is used with the additional softmax layer discussed above. In this embodiment, the autoencoder provides consistency in addition to providing an apparent age as an output. For example, consistency is achieved when similar images or CT scans provide similar apparent ages or ŷ as an output. As known to one skilled in the art, an autoencoder can have an input layer, an output layer, and a number of one or more hidden layer connecting them, where the output layer has the same number of nodes as the input layer. The purpose of the autoencoder is to reconstruct the inputs to minimize the difference between the input and the output instead of predicting target value. As depicted in FIG. 6, the autoencoder is an inverse deep learning network. In FIG. 6, the input layer consumes images 49 and the output image is produced by inverse network 64.

FIG. 7 is illustration of a schematic diagram 700 of a method of unsupervised deep learning for training apparent spine age program 11 using soft labels, in accordance with at least one embodiment of the invention FIG. 7 provides schematic diagram 700 depicting additional details of the method of training deep learning network 70 using unsupervised training with reference to step 412 of FIG. 4. As depicted, FIG. 7 includes images 49, deep learning network 70, softmax spine age classes 72*a*-72*n*, and equation (1), where equation (1) is the objective function for the softmax regression with minimum entropy. Deep learning network 70 can receive large amounts of image data (e.g., hundreds or thousands of images) of CT scans, CT volumes, or MRI scans from CT scanner 15, MRI scanner 5, or another source from which image data of spines or portions of spines may be extracted by apparent spine age program 11 for unsupervised training of deep learning network 70. The image data extracted may be two-dimensional or three-dimensional portions of a spine or of a complete spine, using the methods discussed earlier with respect to FIG. 4. FIG. 7 is an example of a softmax regression network for soft labelling. In other embodiments, deep learning network 70 receives hundreds or thousands of CT scans, CT volumes, or MRI scans from which two-dimension or three-dimensional sections of a vertebra or a disc can be extracted for training of deep learning network 70 in apparent spine age program 11.

In equation (1), L(q,y) is the loss function, β is a hyperparameter that has value from 0-1, and $q_k$ is a probability of class k as determined by deep learning network 70 (e.g., the output of softmax layer which is the last layer of deep learning network 70). In various embodiments, the optimal value of β is determined during the training. This method of training of apparent spine age program 11 can be applied to images of a complete spine, two-dimensional or three-dimensional sections of a portion of the spine, two-dimensional or three-dimensional sections of a vertebra or a disc.

In an embodiment, apparent spine age program 11 using a setup with a single softmax layer as depicted in FIG. 7, the objective function for the softmax regression with minimum entropy conditions is illustrated in equation (1), where $q_k$ is a probability of class k that is the output of the softmax layer that is the last layer of deep learning network 70, β is a hyperparameter with a value between 0 and 1 (e.g., the optimal value of β is determined during training), and $y_k$ is either 0 or 1 depending on the chronological age of the subject. In equation (1), the summation for the function goes from 18 to 100 since the subject ages are assumed to be between 18 and 100 years old.

FIG. 8 is a block diagram depicting components of a computer system 800 suitable for executing apparent age program 11, in accordance with at least one embodiment of the invention. FIG. 8 depicts a computer system 800, which is representative of computer 10, in accordance with an illustrative embodiment of the present invention. It should be appreciated that FIG. 8 provides only an illustration of one implementation and does not imply any limitations with regard to the environments in which different embodiments may be implemented. The components of computer system of FIG. 8 are suitable for executing apparent age program 11. Many modifications to the depicted environment may be made. The computer system of FIG. 8 includes processor(s) 801, cache 803, memory 802, persistent storage 805, communications unit 807, input/output (I/O) interface(s) 806, and communications unit 807. Communications unit 807 provides communications between cache 803, memory 802, persistent storage 805, communications unit 807, and input/output (I/O) interface(s) 806. Communications unit 807 can be implemented with any architecture designed for passing data and/or control information between processors (such as microprocessors, communications and network processors, etc.), system memory, peripheral devices, and any other hardware components within a system. For example, communications unit 807 can be implemented with one or more buses or a crossbar switch.

Memory 802 and persistent storage 805 are computer readable storage media. In this embodiment, memory 802 includes random access memory (RAM). In general, memory 802 can include any suitable volatile or non-volatile computer readable storage media. Cache 803 is a fast memory that enhances the performance of processor(s) 801 by holding recently accessed data, and data near recently accessed data, from memory 802. In various embodiments, memory 802 and persistent storage 805 may store data including the results of apparent age program 11, CT scan data, and/or MRI scan data.

Program instructions and data (e.g., software and data 810) used to practice embodiments of the present invention may be stored in persistent storage 805 and in memory 802 for execution by one or more of the respective processor(s) 801 via cache 803. In an embodiment, persistent storage 805 includes a magnetic hard disk drive. Alternatively, or in addition to a magnetic hard disk drive, persistent storage 805 can include a solid state hard drive, a semiconductor storage device, a read-only memory (ROM), an erasable programmable read-only memory (EPROM), a flash memory, or any other computer readable storage media that is capable of storing program instructions or digital information.

The media used by persistent storage 805 may also be removable. For example, a removable hard drive may be used for persistent storage 805. Other examples include optical and magnetic disks, thumb drives, and smart cards that are inserted into a drive for transfer onto another computer readable storage medium that is also part of persistent storage 805. Software and data 810 can be stored in persistent storage 805 for access and/or execution by one or more of the respective processor(s) 801 via cache 803.

Communications unit 807, in these examples, provides for communications with other data processing systems or devices. In these examples, communications unit 807 includes one or more network interface cards. Communications unit 807 may provide communications through the use of either or both physical and wireless communications links using communication fabric 804. Program instructions and data (e.g., software and data 810) used to practice embodiments of the present invention may be downloaded to persistent storage 805 through communications unit 807.

I/O interface(s) 806 allows for input and output of data with other devices that may be connected to each computer system. For example, I/O interface(s) 806 may provide a connection to external device(s) 808, such as a keyboard, a keypad, a touch screen, and/or some other suitable input device. External device(s) 808 can also include portable computer readable storage media, such as, for example, thumb drives, portable optical or magnetic disks, and memory cards. Program instructions and data (e.g., software and data 810) used to practice embodiments of the present invention can be stored on such portable computer readable storage media and can be loaded onto persistent storage 805 via I/O interface(s) 806. I/O interface(s) 806 also connect to display 809.

Display 809 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute a resource entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method, the computer-implemented method comprising:
   receiving, by one or more computer processors, image data of a subject including at least a portion of a spine of the subject and a chronological age of the subject;
   pre-processing, by one or more computer processors, the image data including at least the portion of a spine; and
   determining, by one or more computer processors, an apparent age of one of the spine or the portion of the spine of the subject using a trained artificial intelligence deep learning algorithm at least by:
      retrieving, by one or more computer processors, a plurality of spine image data of a plurality of subjects for training the artificial intelligence deep learning algorithm;
      pre-processing, by one or more computer processors, the plurality of the spine image data of the plurality of subjects; and
      training, by one or more computer processors, a machine learning algorithm using unsupervised deep learning wherein, the machine learning algorithm is a deep learning network wherein, a latent variable indicates an apparent spine age, the chronological age of the subject is a random variable derived from a distribution of a plurality of probabilities of the chronological age with respect to the apparent age and wherein the deep learning network learns the distribution of the plurality of probabilities chronological age with respect to the apparent age from the training using the plurality of image data.

2. The computer-implemented method of claim 1, wherein receiving the image data of the subject including at least a portion of the spine of the subject includes receiving one of a computed tomography (CT) scan, a CT volume, or a magnetic resonance imaging (MRI) scan of at least a portion of the spine of the subject.

3. The computer-implemented method of claim 2, wherein pre-processing the image data including at least a portion of the spine of the subject includes extracting one of the spine or the portion of the spine from one of the CT scan, the CT volume, or a MRI scan.

4. The computer-implemented method of claim 3, wherein the spine or the portion of the spine extracted from the image data is one of a two-dimensional section or a three-dimensional section of the spine or the portion of the spine, and wherein the portion of the spine includes one of a vertebra, a disc, or a combination of more than one vertebra and one or more disc of the spine of the subject.

5. The computer-implemented method of claim 1, wherein training the machine learning algorithm using unsupervised deep learning includes using a deep learning network with an additional softmax layer on top of a last densely connected softmax layer.

6. The computer-implemented method of claim 5, wherein training the machine learning algorithm using unsupervised deep learning comprises adding an inverse deep learning network as an autoencoder.

7. The computer-implemented method of claim 1, wherein training the machine learning algorithm using unsupervised deep learning includes using soft labelling and minimum entropy with a softmax regression.

8. The computer-implemented method of claim 1, further comprising adding a notation of excessive spinal degeneration associated with one of the spine or the portion of the spine to an output in response to the apparent age of one of the spine or a portion of the spine of the subject is greater than the chronological age of the subject by more than a pre-set number of years.

9. A computer program product for determining an apparent spine age, the computer program product comprising:
   one or more computer readable storage media; and
   program instructions stored on the one or more computer readable storage media, the program instructions executable by a processor, the program instructions comprising instructions for:
      receiving image data of a subject including at least a portion of a spine of the subject and a chronological age of the subject;
      pre-processing the image data including at least the portion of a spine; and determining an apparent age of one of the spine or the portion of the spine of the subject using a trained artificial intelligence deep learning algorithm at least by:
retrieving, by one or more computer processors, a plurality of spine image data of a plurality of subjects for training the artificial intelligence deep learning algorithm;
pre-processing, by one or more computer processors, the plurality of the spine image data of the plurality of subjects; and
training, by one or more computer processors, a machine learning algorithm using unsupervised deep learning wherein, the machine learning algorithm is a deep learning network wherein, a latent variable indicates an apparent spine age, the chronological age of the subject is a random variable derived from a distribution of a plurality of probabilities of the chronological age with respect to the apparent age and wherein the deep learning network learns the distribution of the plurality of probabilities chronological age with respect to the apparent age from the training using the plurality of image data.

10. The computer program product of claim 9, wherein receiving the image data of the subject including at least a portion of the spine of the subject includes receiving one of a computed tomography (CT) scan, a CT volume, or a magnetic resonance imaging (MRI) scan of at least a portion of the spine of the subject.

11. The computer program product of claim 10, wherein pre-processing the image data including at least a portion of the spine of the subject includes extracting one of the spine or the portion of the spine from one of the CT scan, the CT volume, or a MRI scan.

12. The computer program product of claim 11, wherein the spine or the portion of the spine extracted from the image data is one of a two-dimensional section or a three-dimensional section of the spine or the portion of the spine, and wherein the portion of the spine includes one of a vertebra, a disc, or a combination of more than one vertebra and one or more disc of a spine of the subject.

13. The computer program product of claim 9, wherein training the machine learning algorithm using unsupervised deep learning includes using a deep learning network with an additional softmax layer on top of a last densely connected softmax layer.

14. The computer program product of claim 13, wherein training the machine learning algorithm using unsupervised deep learning comprises adding an inverse deep learning network as an autoencoder.

15. The computer program product of claim 9, wherein training the machine learning algorithm using unsupervised deep learning includes using soft labelling and minimum entropy with a softmax regression.

16. The computer program product of claim 9, further comprising adding a notation of excessive spinal degeneration associated with one of the spine or the portion of the spine to an output in response to the apparent age of one of the spine or a portion of the spine of the subject is greater than the chronological age of the subject by more than a pre-set number of years.

17. A computer system comprising:
one or more computer processors;
one or more computer readable storage media;
program instructions stored on the one or more computer readable storage media for execution by at least one of the one or more processors, the program instructions comprising instructions to perform:
receiving image data of a subject including at least a portion of a spine of the subject and a chronological age of the subject;
pre-processing the image data including at least the portion of a spine; and
determining an apparent age of one of the spine or the portion of the spine of the subject using a trained artificial intelligence deep learning algorithm at least by:
retrieving, by one or more computer processors, a plurality of spine image data of a plurality of subjects for training the artificial intelligence deep learning algorithm;
pre-processing, by one or more computer processors, the plurality of the spine image data of the plurality of subjects; and
training, by one or more computer processors, a machine learning algorithm using unsupervised deep learning wherein, the machine learning algorithm is a deep learning network wherein, a latent variable indicates an apparent spine age, the chronological age of the subject is a random variable derived from a distribution of a plurality of probabilities of the chronological age with respect to the apparent age and wherein the deep learning network learns the distribution of the plurality of probabilities chronological age with respect to the apparent age from the training using the plurality of image data.

18. The computer system of claim 17, wherein training the machine learning algorithm using unsupervised deep learning includes using a deep learning network with an additional softmax layer on top of a last densely connected softmax layer.

19. The computer system of claim 17, wherein training the machine learning algorithm using unsupervised deep learning includes using soft labelling and minimum entropy with a softmax regression.

20. The computer system of claim 17, further comprising adding a notation of excessive spinal degeneration associated with one of the spine or the portion of the spine to an output in response to the apparent age of one of the spine or a portion of the spine of the subject is greater than the chronological age of the subject by more than a pre-set number of years.

* * * * *